US005641674A

United States Patent [19]

Dehoux et al.

[11] Patent Number: 5,641,674
[45] Date of Patent: Jun. 24, 1997

[54] NUCLEOTIDE SEQUENCES AND PROTEINS CONFERRING CYCLOHEXIMIDE RESISTANCE

[75] Inventors: Pierre Dehoux; Julian Davies, both of Paris, France

[73] Assignee: Institut Pasteur, Paris Cedex, France

[21] Appl. No.: 175,388

[22] PCT Filed: Jul. 15, 1992

[86] PCT No.: PCT/FR92/00685

§ 371 Date: Jun. 9, 1994

§ 102(e) Date: Jun. 9, 1994

[87] PCT Pub. No.: WO93/02201

PCT Pub. Date: Feb. 4, 1993

[30] Foreign Application Priority Data

Jul. 15, 1991 [FR] France .................................. 91 08906

[51] Int. Cl.$^6$ .......................... C12N 15/31; C12N 15/81; C12N 15/82

[52] U.S. Cl. ........................ 435/6; 435/254.2; 435/320.1; 435/325; 435/419; 530/371; 536/23.74

[58] Field of Search ......................... 536/23.74; 530/350, 530/371; 435/320.1, 240.1, 240.2, 240.4, 254.2

*Primary Examiner*—Keith D. Hendricks
*Attorney, Agent, or Firm*—Oblon, Spivak, McClelland, Maier & Neustadt, P.C.

[57] ABSTRACT

The invention relates to a nucleotide sequence coding for a cycloheximide resistance protein sensitive to concatenation of amino acids A, or coding for all or part of said optionally modified concatenation A, in as much as the formed protein confers cycloheximide resistance to a recombinant eucaryotic host transformed by the nucleotide sequence coding for said protein, in conditions appropriate for its production. The invention also relates to a sequence containing the DNA coding for the concatenation A and capable of conferring a high level of resistance to cycloheximide in a given host.

24 Claims, 5 Drawing Sheets

```
         10         20         30         40         50         60
   1  CCTCGAGGTC GACATTCAAG GGTTAGTAT  CCTGAAAACA AAGCTTGTAT AGACAGCCGA    60
  61  CGGTTCTTGG TGACTGTTTG CATCCGTGCA CCATAAAATC TCTCTTAACC ACCCACACAT   120
 121  TGATTTCGT  GTCAATTGA  AATGTGAAAA ATAAAATTGT TTCCCAATTA GGACTATATT   180
 181  CGTCTGTGGG AAAATAACAT TGCCTAGTGG CATTGGTGTG GCCTAACCAG GCCGAATCAC   240
 241  TCACTTCCA  CTAACAGACC TTCCTCCTGG TCGGTCTGGT CTGGGCTACC GGCAGTGTAG   300
 301  TCTCTCTTGC CAACACATTA CGCATTCATG CTTGCTTCTG CCTACTGCTT CCCCGCCCAG   360
 361  GCTAAGCTTG GACGTGCGTA GTCGGGGGGC CAGTAACGCC TGCTCGTCTG GACTTGTTCG   420
 421  CCTTCACTCT TGCTGCCGTC TCTGCTTCGA TGGCTGCCAT TCGGCAATTC TCATCTGGAA   480
 481  GGATTGAACC ACCTTGAATT TTTCAACATT AAAATATTAC ACAAGGAAAG TTCATCATAG   540
 541  TAGATATATC GTATAGTTGA TTGTTATAGC ACCTATTTGT TTCAGTACAT TCAGAAAGCG   600
 601  TAACTCAACA GAGATCAAAT CAGTCACAAT GGGTATGTGA ACAAGATTTA AAATATACCG   660
 661  TGGAGATTGT CAGTGGTTTA TTCGATTTT  GGTATCCTGA GGGAAGAATG GAACGTTTGA   720
 721  AGTTTAGTAC CAAGTGAACA TGAAATGAGC TATGGTTATT TAACAGAATA CAGCATTTCA   780
 781  GAGTGAATCA ATGAGAAAAC ACCAACCGTA TTGGAAATTC AGATATTGCA TCGACAAGGG   840
 841  GGGAGAGTTC ATTTGAGTTG GTGAACTATA TCAAAAGATC AGTATTTTGG TCGAAGTATG   900
 901  GACGATTCAC TAGCATAAAA CCCTGTTCAC GCTGGAGGAA GTAATGTGGG TTATTTGTTG   960
 961  TCCCTATGTT TCTTAATTCG GTGTAGTCGA GACAACCTCA GAGAATTGTA TATCAGTGAA  1020
1021  GTCAACGCTA CACTGACTGA ACATAATTAA CAGGAACTCA GTCGTATTAA ACAACTGGGG  1080
1081  TTCAGATAGC CTGACCTCC  CTATACAATA AGAAGAAGAG AATAGAATTC CTGCAATCAA  1140
1141  AATAAGCTGG ATGAAGCTAA AGAATATTTT TTTACTAACA TCGACATGTA TCACTATCTT  1200
```

FIG. 2A

```
1201  ATGATATGTT AATTTCTAAC AGTTAACGTT CCAAAGACCA GAAAGACTTA CTGTAAGGGT  1260
1261  AAGGAGTGCC GTAAGCACGC CCAACACAAG GTACCCAAT  ACAAGGCTGG TAAGGCTTCC  1320
1321  TTGTACGCTC AAGGTAAGAG AAGATATGAC CGTAAACAAT CTGGTTTCGG TGGTCAAACC  1380
1381  AAGCAAATTT TCCACAAGAA AGCTAAGACT ACCAAGAAGG TCGTTTTGAG ATTGGAATGT  1440
1441  ATGTCCTGTA AGACCAAGAC CCAATTGGCT TTGAAGAGAT GTAAGCACTT CGAATTGGGT  1500
1501  GGTGAAAAGA AGCAAAAAGG TCAAGCTTTG CAATTCTGAG ATTATCTTTT GGAAGACCAT  1560
1561  TTGTACCAA  TTTGTCAATT TTTTAACTTT TCTATAAGTA TTACGAATTC ACATATACTC  1620
1621  TTTCATCACA TTTATAATCT CATATCTGTC ATTGTATAG  TTTAGTCTCC ACTGGGTACT  1680
1681  TCTTCACTTT GCGATTTGTA TTATACGTAT TCTAAGTATA ATTTTCAGCA GAACGCATAA  1740
1741  GAGTTTATTA ACAAGAATTG TTTACAAAGA ATAGGTAGG  ACTCAGGCTA CATTATTGAT  1800
1801  CCTGCAGGCA GTAAAGCTTA CATATGACCT TAGCTAAATAT AACATGTACA TACTCACCAT  1860
1861  GTATACCACT TTTTCATTC  CATTGTCTAA AATAIGTTTT CAAACTTGC  CAAAATCGCC  1920
1921  AATTTCATTG GAAAAACAAA AACATCGAAT CAAACTGAAT TCACGTCAAC TTAGAAAACA ACGAACATGA  1980
1981  AACTATACTG TTAACGTTTA GAGACATATT TCACGGTGG  ATATCGAAT  AAGGCCGTTT GGACGTCGCT  2040
2041  ACTCAGCAA  CAACACGTAA TGTACGGTGG ATATTCGAAT CAGAACTACT ATCAACAGCC  2100
2101  TTCTGGTCGT CCGAAACGAT TTCAGCAAC  TATATGAAAC AGGGAAACAT GCCCTTTCG  GAACTTCTC   2160
2161  AGCCCATGTT CAGCACCAAT TATATGAAAC AACAAGGATC ACAGCCGTCT TACAAGACCG  2220
2221  TCTGACCCAA CAGCAATCGC AACCTCAGTC GCATAATAAT CAATATTATC CGAATGGAGG  2280
2281  GTTACTGAT  GTGCCCAACT TGAATTATCC AGCGACTCCA CCACCAACTC AAAGCATTTA  2340
```

*FIG. 2B*

```
2341  TTCACATAAC AACAACTCTA ATTCGAAGGT ATATCAATCC GCTCAGCATA CATCTCCCGG  2400
2401  TCAATATTCT GTTGCCAGTG AGTCCGGTTT GTACATCCCG CCACCACTGC AGCAACAGCA  2460
2461  GAATGGTCAA CAGAGTCCTG TGAGATCGGT ACATCAACAG ACACAGCAAA CACCGCCAAC  2520
2521  ATTTACTCAG CAACAAAGCT CTCCCAACC TCAGTCACCT CAACACAATA CGTTATCATG  2580
2581  CACAGCAGCA GCAGCAGCAG AACAACAAAC TCAACAGGCC CAGCAGCAAG  2640
2641  GACAACGACA AACTCAGCAA CAGTCTCAGC AGCAAGCTCA ACAACAGAAT GGATCGGCGA  2700
2701  ATAATTACAT GTATTTTGAG AGAAGACCTG ACCTATTGAC CAAAACTACC CAAGACAAAG  2760
2761  CAGATCGAAT TCCTGCAGCC CGGGGATCC ACTAGTTCTA GAGCGGCCGC CACCGGGGTG  2820
2821  GAGCTCCAAT TCGCCCTATA GT                                          2842
          |       |       |       |       |       |
          10      20      30      40      50      60
```

FIG. 2C

1/1
Met val asn val pro lys thr arg lys thr tyr cys lys gly lys glu cys arg lys his
                                            31/11
61/21
ala gln his lys val thr gln tyr lys gly lys ala ser leu tyr ala gln gly lys
                                            91/31
121/41
arg arg tyr asp arg lys gln ser gly phe gly gly gln thr lys gln ile phe his lys
                                            151/51
181/61
lys ala lys thr thr lys lys val val leu arg leu glu cys met ser cys lys thr lys
                                            211/71
241/81
thr gln leu ala leu lys arg cys lys his phe glu leu gly gly gly glu lys lys gln lys
                                            271/91
301/101
gly gln ala leu gln phe OPA

*FIG. 4*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 106 amino acids
        ( B ) TYPE: amino acid
        ( C ) STRANDEDNESS: single (D) TOPOLOGY: unknown (ii) MOLECULE TYPE: protein (xi) SEQUENCE DESCRIPTION: SEQ ID NO:1:

| Met | Val | Asn | Val | Pro | Lys | Thr | Arg | Lys | Thr | Tyr | Cys | Lys | Gly | Lys | Glu |
| 1 | | | | 5 | | | | | 10 | | | | | 15 | |

| Cys | Arg | Lys | His | Ala | Gln | His | Lys | Val | Thr | Gln | Tyr | Lys | Ala | Gly | Lys |
| | | | 20 | | | | | 25 | | | | | 30 | | |

| Ala | Ser | Leu | Tyr | Ala | Gln | Gly | Lys | Arg | Arg | Tyr | Asp | Arg | Lys | Gln | Ser |
| | | | 35 | | | | 40 | | | | | 45 | | | |

| Xaa | Phe | Gly | Gly | Gln | Thr | Lys | Gln | Ile | Phe | His | Lys | Lys | Ala | Lys | Thr |
| | | 50 | | | | | 55 | | | | | 60 | | | |

| Thr | Lys | Lys | Val | Val | Leu | Arg | Leu | Glu | Cys | Met | Ser | Cys | Lys | Thr | Lys |
| 65 | | | | | 70 | | | | | 75 | | | | | 80 |

| Thr | Gln | Leu | Ala | Leu | Lys | Arg | Cys | Lys | His | Phe | Glu | Leu | Gly | Gly | Glu |
| | | | | 85 | | | | | 90 | | | | | 95 | |

| Lys | Lys | Gln | Lys | Gly | Gln | Ala | Leu | Gln | Phe |
| | | | 100 | | | | | 105 | |

(2) INFORMATION FOR SEQ ID NO:2:

(i) SEQUENCE CHARACTERISTICS:
      (A) LENGTH: 321 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:2:

| ATGGTTAACG | TTCCAAAGAC | CAGAAAGACT | TACTGTAAGG | GTAAGGAGTG | CCGTAAGCAC | 60 |
| GCCCAACACA | AGGTTACCCA | ATACAAGGCT | GGTAAGGCTT | CCTTGTACGC | TCAAGGTAAG | 120 |
| AGAAGATATG | ACCGTAAACA | ATCTGGTTTC | GGTGGTCAAA | CCAAGCAAAT | TTTCCACAAG | 180 |
| AAAGCTAAGA | CTACCAAGAA | GGTCGTTTTG | AGATTGGAAT | GTATGTCCTG | TAAGACCAAG | 240 |
| ACCCAATTGG | CTTTGAAGAG | ATGTAAGCAC | TTCGAATTGG | GTGGTGAAAA | GAAGCAAAAG | 300 |
| GGTCAAGCTT | TGCAATTCTG | A | | | | 321 |

(2) INFORMATION FOR SEQ ID NO:3:

(i) SEQUENCE CHARACTERISTICS:
      (A) LENGTH: 2842 base pairs
      (B) TYPE: nucleic acid
      (C) STRANDEDNESS: double
      (D) TOPOLOGY: unknown (ii) MOLECULE TYPE: DNA (genomic)

(xi) SEQUENCE DESCRIPTION: SEQ ID NO:3:

| CCTCGAGGTC | GACATTCAAG | GGTTTAGTAT | CCTGAAAACA | AGCTTGTAT | AGACAGCCGA | 60 |
| CGGTTCTTGG | TGACTGTTTG | CATCCGTGCA | CCATAAAATC | TCTCTTAACC | ACCCACACAT | 120 |
| TGATTTTCGT | GTTCAATTGA | AATGTGAAAA | ATAAAATTGT | TTCCCAATTA | GGACTATATT | 180 |
| CGTCTGTGGG | AAAATAACAT | TGCCTAGTGG | CATTGGTGTG | GCCTAACCAG | GCCGAATCAC | 240 |
| TCACTTTCCA | CTAACAGACC | TTCCTCCTGG | TCGGTCTGGT | CTGGGCTACC | GGCAGTGTAG | 300 |
| TCTCTCTTGC | CAACACATTA | CGCATTCATG | CTTGCTTCTG | CCTACTGCTT | CCCCGCCCAG | 360 |
| GCTAAGCTTG | GACGTGCGTA | GTCGGGGGGC | CAGTAACGCC | TGCTCGTCTG | GACTTGTTCG | 420 |
| CCTTCACTCT | TGCTGCCGTC | TCTGCTTCGA | TGGCTGCCAT | TCGGCAATTC | TCATCTGGAA | 480 |

```
GGATTGAACC ACCTTGAATT TTTCAACATT AAAATATTAC ACAAGGAAAG TTCATCATAG    540
TAGATATATC GTATAGTTGA TTGTTATAGC ACCTATTTGT TTCAGTACAT TCAGAAAGCG    600
TAACTCAACA GAGATCAAAT GAGTCACAAT GGGTATGTGA ACAAGATTTA AAATATACCG    660
TGGAGATTGT CAGTGGTTTA TTCGATTTTT GGTATCCTGA GGGAAGAATG GAACGTTTGA    720
AGTTAGTAC CAAGTGAACA TGAAATGAGC TATGGTTATT TAACAGAATA CAGCATTTCA    780
GAGTGAATCA ATGAGAAAAC ACCAACCGTA TTGGAAATTC AGATATTGCA TCGACAAGGG    840
GGGAGAGTTC ATTTGAGTTG GTGAACTATA TCAAAGATC AGTATTTTGG TCGAAGTATG    900
GACGATTCAC TAGCATAAAA CCCTGTTCAC GCTGGAGGAA GTAATTTGGG TTATTTGTTG    960
TCCCTATGTT TCTTAATTCG GTGTAGTCGA GACAACCTCA GAGAATTGTA TATCAGTGAA   1020
GTCAACGCTA CACTGACTGA ACATAATTAA CAGGAACTCA GTCGTATTAA CAACTGGGG   1080
TTCAGATAGC CTGGACCTCC CTATACAATA GAAGAAGAG AATAGAATTC CTGCAATCAA   1140
AATAAGCTGG ATGAAGCTAA AGAATATTTT TTACTAACA TCGACATGTA TCACTATCTT   1200
ATGATATGTT AATTTCTAAC AGTTAACGTT CCAAAGACCA GAAAGACTTA CTGTAAGGGT   1260
AAGGAGTGCC GTAAGCACGC CAACACAAG GTTACCCAAT ACAAGGCTGG TAAGGCTTCC   1320
TTGTACGCTC AAGGTAAGAG AAGATATGAC CGTAAACAAT CTGGTTTCGG TGGTCAAACC   1380
AAGCAAATTT TCCACAAGAA AGCTAAGACT ACCAAGAAGG TCGTTTTGAG ATTGGAATGT   1440
ATGTCCTGTA AGACCAAGAC CCAATTGGCT TTGAAGAGAT GTAAGCACTT CGAATTGGGT   1500
GGTGAAAAGA AGCAAAAGGG TCAAGCTTTG CAATTCTGAG ATTATCTTTT GGAAGACCAT   1560
TTGTTACCAA TTTGTCAATT TTTAACTTT TCTATAAGTA TTACGAATTC ACATATACTC   1620
TTTCATCACA TTTATAATCT CATATCTGTC ATTTGTATAG TTTAGTCTCC ACTGGGTACT   1680
TCTTCACTTT GCGATTGTA TTATACGTAT TCTAAGTATA ATTTCAGCA GAACGCATAA   1740
GAGTTTATTA ACAAGAATTG TTACAAAGA ATAGCGTAGG ACTCAGGCTA CATTATTGAT   1800
CCTGCAGGCA GTAAAGCTTA CATATGACCT TAGCTAATAT AACATGTACA TACTCACCAT   1860
GTATACCACT TTTTTCATTC CATTGTCTAA AATATGTTTT CAATATTTGC CAAAATCGCC   1920
AATTTCATTG GAAAAACAAA AACATCGAAT CAAACTTGTT TTAGAAAACA ACGAACATGA   1980
AACTATACTG TTAACGTTTA GAGACATATT TCACGTCAAC AAGGCCGTTT GGACGTCGCT   2040
ACTTCAGCAA CAACACGTAA TGTACGGTGG ATATTCGAAT CAGAACTACT ATCAACAGCC   2100
TTCTGGTCGT CCGAAACGAT TTTCAGCAAC AGGGAAACAT GCCCTTTTCG GAACCTTCTC   2160
AGCCCATGTT CAGCACCAAT TATATGAAAC AACAAGGATC ACAGCCGTCT TACAAGACCG   2220
TCTGACCCAA CAGCAATCGC AACCTCAGTC GCATAATAAT CAATATTATC CGAATGGAGG   2280
GTTACTGAT GTGCCCAACT TGAATTATCC AGCGACTCCA CCACCAACTC AAAGCATTTA   2340
TTCACATAAC AACAACTCTA ATTCGAAGGT ATATCAATCC GCTCAGCATA CATCTCCCGG   2400
TCAATATTCT GTTGCCAGTG AGTCCGGTTT GTACATCCCG CCACCACTGC AGCAACAGCA   2460
GAATGGTCAA CAGAGTCCTG TGAGATCGGT ACATCAACAG ACACAGCAAA CACCGCCAAC   2520
ATTACTCAG CAACAAAGCT CTTCCCAACC TCAGTCACCT CAACACAATA CGTTATCATG   2580
CACAGCAGCA GCAGCAGCAG CAGCAGCAGC AACAACAAAC TCAACAGGCC CAGCAGCAAG   2640
GACAACGACA AACTCAGCAA CAGTCTCAGC AGCAAGCTCA ACAACAGAAT GGATCGGCGA   2700
ATAATTACAT GTATTTGAG AGAAGACCTG ACCTATTGAC CAAAACTACC CAAGACAAAG   2760
CAGATCGAAT TCCTGCAGCC CGGGGGATCC ACTAGTTCTA GAGCGGCCGC CACCGCGGTG   2820
```

```
GAGCTCCAAT TCGCCCTATA GT                                                    2842
```

NUCLEOTIDE SEQUENCES AND PROTEINS CONFERRING CYCLOHEXIMIDE RESISTANCE

BACKGROUND OF THE INVENTION

The invention relates to nucleotide sequences capable of conferring resistance to cyloheximide, cycloheximide resistance proteins and their use as selection markers, for example, to monitor nucleic acid transfer.

DESCRIPTION OF THE RELATED ART

The inventors have, in fact, investigated selectionmarkers suitable for monitoring nudeic acid transfer in eukaryotes, markers which might be more efficient than the markers usually used which are derived from prokaryotic organisms. It is know for example that the markers usually used (geneticin G-418, hygromycin and bleomycin) are derived from resistance genes isolated from prokaryotes and are usually rather inefficient, particularly in fungi. These problems oblige experimenters to use very high concentrations of antibiotics which cause toxidty problems and increase production costs Consequently, other selection agents have been used, for example selection by methotrexate, selection by auxotrophy, etc. However, these selection agents are not generally applicable. There is thus a need for the creation of systems suited to the use of a more effident and/or potent marker than the markers known hitherto and at lower production costs.

Cycloheximide might constitute a potentially useful marker for example for detecting the transfer of heterologous nudeic acid in eukaryotes. For this purpose, the eukaryotes which it is desired to modify in a controllable manner by means of a detection test for resistance to cycloheximide, must be made resistant to this antibiotic under satisfactory conditions in order to ensure reliable monitoring of the transfer of a heterologous nucleic acid made either for research purposes or for the purpose of industrial exploitation.

Cycloheximide is an antibiotic which inhibits protein synthesis by binding to the 60S ribosomal subunit as described by STOCKLEIN et al. (1980, Curt. Genetics 1, 177–183).

Eukaryotic organisms naturally resistant to cycloheximide are rare, up to now observations relating to the mechanisms of resistance have bean described in a mutant of an organism naturally sensitive to cycloheximide, the cyh2 mutant of the yeast *Saccharomyces cerevisiae*. In this context, the phenomenon of resistance is created by a modification of the ribosomal protein L29 (STOCKLEIN et al., 1980).

These mutant cellular organisms are usually resistant to low concentrations of cycloheximide (of the order of 5–10 µg/ml).

Other authors (TAKAGI et al. in the U.S. Pat. No. 4,857,460) have reported results relating to the study of resistance to cycloheximide in another yeast *Candida maltosa*. They present a DNA sequence conferring resistance to cycloheximide on *C. maltosa*. However, neither gene nor open reading frame was identified in this sequence. In other words, the U.S. Pat. No. 4,857,460 does not give the elements for the characterization of a gene elements which could have led to a definition of the conditions for its use, for example, to transform eukaryotes different from *Candida maltosa* into strains resistant to cycloheximide in a reproducible manner.

SUMMARY OF THE INVENTION

The inventors have concerned themselves with the yeast *Kluyveromyces lactis* (*K. lactis*) and demonstrated the fact that cycloheximide resistance in *K. lactis* depends on the expression of a specific gene. They have also identified the fact that the level of resistance of this yeast to this antibiotic involves other elements linked to the presence of a specific DNA which has the role of cofactor (or cofactor sequence).

In an advantageous embodiment of the invention, the resistance obtained is specific for cycloheximide, the transformed hosts resistant to this antibiotic (cyc$^R$) being sensitive to several classical inhibitors of ribosomal functions (cryptopleurin, blasticidin, trichodermin, anisomycin, hygromycin).

Thus the inventors obtained in *K. lactis* a nucleic acid sequence of about 5.2 kb, capable of conferring a level of resistance to a cell host transformed by this sequence sufficiently high for the creation of a selection system as a result of resistance to this antibiotic, this resistance being expressed at a cycloheximide concentration higher than 1 mg/ml.

Within this nucleic acid sequence the inventors have identified and characterized a specific gene coding for a protein whose presence proves to be necessary for inducing the phenomenon of resistance in *K. lactis*.

This specific gene codes for a ribosomal protein which is responsible for resistance to a cycloheximide concentration of the order of 100 µg/ml. Complete resistance to this antibiotic in *K. lactis* requires not only the presence of this resistance-inducing sequence but also the presence of additional DNA elements contained in the 5.2 kb nucleic acid sequence defined by the inventors and described hereafter. These additional elements play the role of cofactors.

Thus, the subject of the present application is nucleotide sequences as well as a protein which are capable of conferring cycloheximide resistance on a eukaryote cell host naturally sensitive to this antibiotic or resistant to a low concentration of this antibiotic (also designated as low-level resistant organism). This first type of protein will be designated in what follows by the expression "resistance protein".

The invention also relates to a nucleic acid sequence comprising a gene which codes for the resistant protein described above in *K lactis*, as well as sequences determining the presence of cofactors implicated in the level of resistance conferred by the above-mentioned protein.

It also relates to the gene coding for the resistance protein and the different nucleic acid fragments determining the presence of the cofactors.

It also relates to cloning and/or expression vectors for these nucleotide sequences as well as eukaryotic cell hosts transformed by these vectors.

BRIEF DESCRIPTION OF THE DRAWINGS

FIG. 2 depicts a sequence fragment of the DNA of *K. lactis* conferring cycloheximide resistance (SEQ ID NO:3).

FIG. 4 depicts the sequence of the protein conferring cycloheximide resistance encoded by *K. lactis* DNA.

DESCRIPTION OF THE PREFERRED EMBODIMENTS

Figure 1:
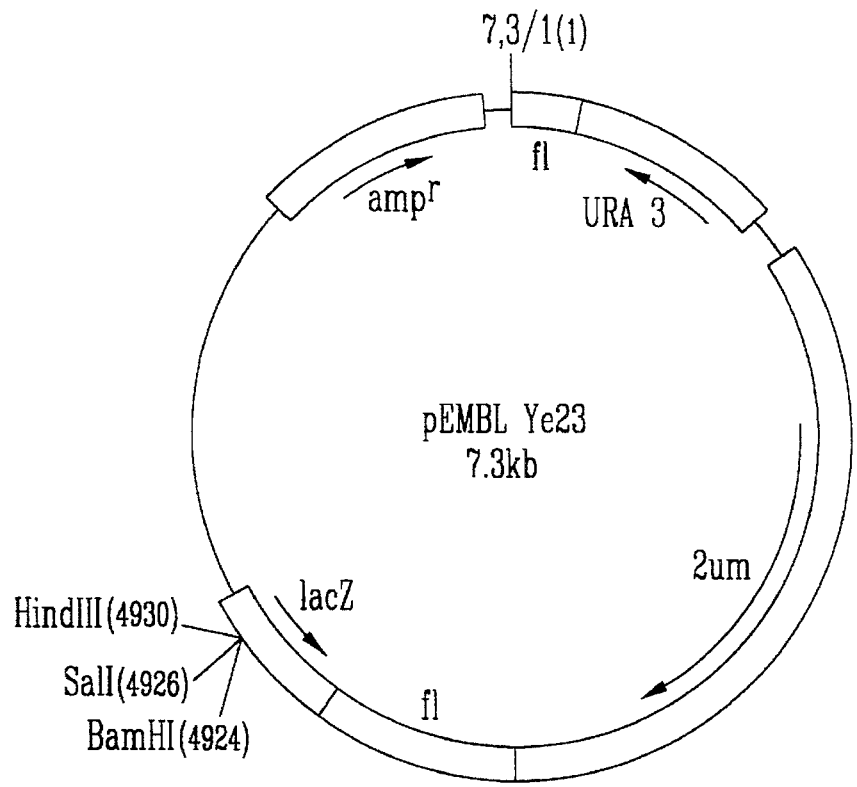
FIG. 1 depicts plasmid pEMBL Ye23, a shuttle vector for *E. coli* and *S. cerevisiae*, into which the genomic library of *K. lactis* strain 2359-152 was inserted.

A first protein according to the invention or cycloheximide resistance protein is a protein whose presence is necessary and sufficient to confer resistance to cycloheximide on a host naturally sensitive to it. It is characterized in that it corresponds to the following amino acid sequence A (SEQ. ID NO:2), or in that it comprises all or part of this sequence A (SEQ ID NO. 1), possibly modified, provided that the protein formed confers cycloheximide resistance on a recombinant eukaryotic host transformed by the nucleotide sequence coding for this protein under conditions allowing its production.

SEQUENCE A:

```
1/1                                         31/11
Met val asn val pro lys thr arg lys thr tyr cys lys gly lys glu cys arg lys his
61/21                                       91/31
ala gln his lys val thr gln tyr lys ala gly lys ala ser leu tyr ala gln gly lys
121/41                                      151/51
arg arg tyr asp arg lys gln ser gly phe gly gly gln thr lys gln ile phe his lys
181/61                                      211/71
lys ala lys thr thr lys lys val val leu arg leu glu cys met ser cys lys thr lys
241/81                                      271/91
thr gln leu ala leu lys arg cys lys his phe glu leu gly gly glu lys lys gln lys
301/101
gly gln ala leu gln phe OPA
```

The property d this protein to confer cycloheximide resistance can be evaluated when it is produced in a specific eukaryotic cell host, naturally sensitive to cycloheximide at concentrations higher than a threshold defined as a function of the nature of the host, and when it allows resistance to be produced in this host at a concentration about 5 to 15 fold higher, and preferably about 10 fold higher, than the cycloheximide concentration conferring the natural sensitivity in this host.

In yeasts, in *S. cerevisiae* in particular, this increase in the resistance level is about 10 fold, even 100 fold to 1000 fold higher than the level observed in the wild type strain.

As examples, the order of magnitude of the natural sensitivity of various organisms to cycloheximide is given below:

yeasts *S. cerevisiae*: 1 µg/ml higher eukaryotic cells: 1 µg/ml tobacco plants: 10 µg/ml.

Generally, the natural sensitivity of a specific organism is expressed as soon the presence of cydoheximide in the culture medium inhibits the growth and multiplication of the organism When reference is made in this text to a eukaryotic host sensitive to cycloheximide, this reference must be interpreted as designating any eukaryotic organism complying with the above definition in regard to cycloheximide resistance.

A cycloheximide resistance protein according to the invention may also be characterized in that it is encoded in the following nucleotide sequence I, by a part of sequence ID NO: 2 or by a modified sequence ID NO: 2, provided that the protein encoded by the partial sequence or this modified sequence is capable of conferring resistance to a concentration equal to at least 100 µg/ml of cycloheximide when it is introduced in a eukaryotic host, for example the yeast *Saccharomyces cerevisiae* under conditions allowing its expression

Sequence I

```
                    AT  GGTTAACGTT  CCAAAGACCA  GAAAGACTTA  CTGTAAGGGT

AAGGAGTGCC  GTAAGCACGC  CCAACACAAG  GTTACCCAAT  ACAAGGCTGG  TAAGGCTTCC

TTGTACGCTC  AAGGTAAGAG  AAGATATGAC  CGTAAACAAT  CTGGTTTCGG  TGGTCAAACC

AAGCAAATTT  TCCACAAGAA  AGCTAAGACT  ACCAAGAAGG  TCGTTTTGAG  ATTGGAATGT

ATGTCCTGTA  AGACCAAGAC  CCAATTGGCT  TTGAAGAGAT  GTAAGCACTT  CGAATTGGGT

GGTGAAAAGA  AGCAAAAGGG  TCAAGCTTTG  CAATTCTGA
```

Figure 3:
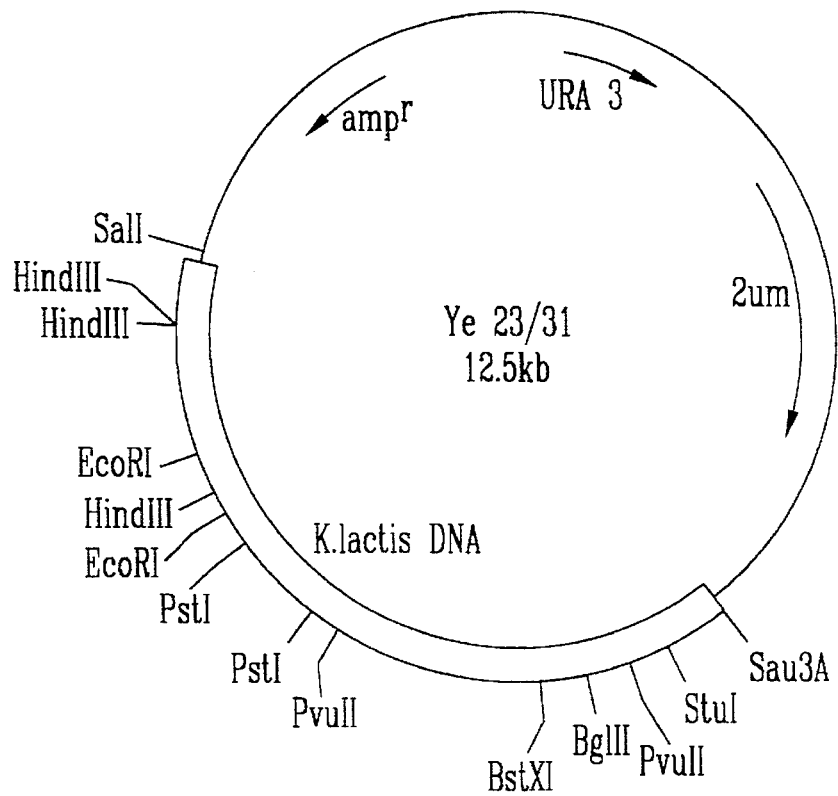
FIG. 3 depicts a restriction map of the 5.2 kb DNA fragment of *K. lactis* which was inserted at the BamHi site of vector Ye23.

The invention also relates to a nucleic acid sequence comprising the sequence coding for the cycloheximide resistance protein in *K. lactis*, this protein being characterized in that it complies with one of the following definitions:

(a) it is a nucleic acid sequence of *K. lactis* of about 5.2 kb capable of conferring cycloheximide resistance to a concentration higher than 1 mg/ml in *K. lactis* or in *S. cerevisiae*, and comprising the restriction sites defined in FIG. 3. The various sites are situated at the following positions:

Sau3A: 0, StuI:+300 bp, PvuII:+600 bp, BglIII: +900 bp, BstXI: 1200 bp, PvuII: +2300, PstI: +2400 bp, PstI: +3000 bp, EcoRI: 3200 bp, HindIII: +3300 bp, EcoRI: +3700 bp, HindIII: +4500 bp, HindIII: +4540 bp, SalI: +5100 bp.

(b) it is a nucleic acid sequence of about 5.2 kb, comprising nucleotide sequence ID NO:2 or hybridizing with the sequence complementary to sequence ID NO: 2 under conditions of high stringency (0.1×SSC, 0.1% SDS at 65° C.), and capable of conferring resistance to a cycloheximide concentration higher than 100 μg/ml, and preferably higher than 1 mg/ml, in *K. lactis*;

(c) it is a nucleic acid sequence of about 5.2 kb, comprising the following nucleotide sequence ID NO:3 or hybridizing with the sequence complementary to sequence ID NO:3 under conditions of high stringency, and capable of conferring resistance to a cycloheximide concentration higher than 100 μg/ml, and preferably higher than 1 mg/ml, in *K. lactis*;

(d) it is a nucleic acid sequence comprising the nucleotide sequence situated between positions 9 and 2763 of sequence ID NO:3 or a sequence hybridizing with the sequence complementary to sequence ID NO:3 under conditions of high stringency, and capable of conferring resistance to a cycloheximide concentration higher than 100 μg/ml, and preferably higher than 1 mg/ml, in *K. lactis*. When a nucleic acid sequence complying with me of the definitions given above is introduced into a yeast such as *S. cerevisiae*, it confers on this yeast resistance to cycloheximide at a concentration higher than 100 μg/ml, this being advantageously expressed for a cycloheximide concentration higher than 1 mg/ml.

SEQUENCE II:

```
        1          10         20         30         40         50         60
  1 CCTCGAGGTC GACATTCAAG GGTTTAGTAT CCTGAAAACA AAGCTTGTAT AGACAGCCGA  60
 61 CGGTTCTTGG TGACTGTTTG CATCCGTGCA CCATAAAATC TCTCTTAACC ACCCACACAT 120
121 TGATTTTCGT GTTCAATTGA AATGTGAAAA ATAAATTGT  TTCCCAATTA GGACTATATT 180
181 CGTCTGTGGG AAAATAACAT TGCCTAGTGG CATTGGTGTG GCCTAACCAG GCCGAATCAC 240
241 TCACTTTCCA CTAACAGACC TTCCTCCTGG TCGGTCTGGT CTGGGCTACC GGCAGTGTAG 300
301 TCTCTCTTGC CAACACATTA CGCATTCATG CTTGCTTCTG CCTACTGCTT CCCCGCCCAG 360
361 GCTAAGCTTG GACGTGCGTA GTCGGGGGGC CAGTAACGCC TGCTCGTCTG GACTTGTTCG 420
421 CCTTCACTCT TGCTGCCGTC TCTGCTTCGA TGGCTGCCAT TCGGCAATTC TCATCTGGAA 480
481 GGATTGAACC ACCTTGAATT TTTCAACATT AAAATATTAC ACAAGGAAAG TTCATCATAG 540
541 TAGATATATC GTATAGTTGA TTGTTATAGC ACCTATTTGT TTCAGTACAT TCAGAAAGCG 600
601 TAACTCAACA GAGATCAAAT GAGTCACAAT GGGTATGTGA ACAAGATTTA AAATATACCG 660
661 TGGAGATTGT CAGTGGTTTA TTCGATTTTT GGTATCCTGA GGGAAGAATG GAACGTTTGA 720
721 AGTTAGTAC  CAAGTGAACA TGAAATGAGC TATGGTTATT TAACAGAATA CAGCATTTCA 780
781 GAGTGAATCA ATGAGAAAAC ACCAACCGTA TTGGAAATTC AGATATTGCA TCGACAAGGG 840
841 GGGAGAGTTC ATTTGAGTTG GTGAACTATA TCAAAAGATC AGTATTTTGG TCGAAGTATG 900
```

-continued
SEQUENCE II:

```
 901 GACGATTCAC TAGCATAAAA CCCTGTTCAC GCTGGAGGAA GTAATTTGGG TTATTTGTTG  960
 961 TCCCTATGTT TCTTAATTCG GTGTAGTCGA GACAACCTCA GAGAATTGTA TATCAGTGAA 1020
1021 GTCAACGCTA CACTGACTGA ACATAATTAA CAGGAACTCA GTCGTATTAA ACAACTGGGG 1080
1081 TTCAGATAGC CTGGACCTCC CTATACAATA AGAAGAAGAG AATAGAATTC CTGCAATCAA 1140
1141 AATAAGCTGG ATGAAGCTAA AGAATATTTT TTTACTAACA TCGACATGTA TCACTATCTT 1200
1201 ATGATATGTT AATTTCTAAC AGTTAACGTT CCAAAGACCA GAAAGACTTA CTGTAAGGGT 1260
1261 AAGGAGTGCC GTAAGCACGC CCAACACAAG GTTACCCAAT ACAAGGCTGG TAAGGCTTCC 1320
1321 TTGTACGCTC AAGGTAAGAG AAGATATGAC CGTAAACAAT CTGGTTTCGG TGGTCAAACC 1380
1381 AAGCAAATTT TCCACAAGAA AGCTAAGACT ACCAAGAAGG TCGTTTTGAG ATTGGAATGT 1440
1441 ATGTCCTGTA AGACCAAGAC CCAATTGGCT TTGAAGAGAT GTAAGCACTT CGAATTGGGT 1500
1501 GGTGAAAAGA AGCAAAAGGG TCAAGCTTTG CAATTCTGAG ATTATCTTTT GGAAGACCAT 1560
1561 TTGTTACCAA TTTGTCAATT TTTTAACTTT TCTATAAGTA TTACGAATTC ACATATACTC 1620
1621 TTTCATCACA TTTATAATCT CATATCTGTC ATTTGTATAG TTTAGTCTCC ACTGGGTACT 1680
1681 TCTTCACTTT GCGATTTGTA TTATACGTAT TCTAAGTATA ATTTTCAGCA GAACGCATAA 1740
1741 GAGTTTATTA ACAAGAATTG TTTACAAAGA ATAGCGTAGG ACTCAGGCTA CATTATTGAT 1800
1801 CCTGCAGGCA GTAAAGCTTA CATATGACCT TAGCTAATAT AACATGTACA TACTCACCAT 1860
1861 GTATACCACT TTTTTCATTC CATTGTCTAA AATATGTTTT CAATATTTGC CAAAATCGCC 1920
1921 AATTTCATTG GAAAAACAAA AACATCGAAT CAAACTTGTT TTAGAAAACA ACGAACATGA 1980
1981 AACTATACTG TTAACGTTTA GAGACATATT TCACGTCAAC AAGGCCGTTT GGACGTCGCT 2040
2041 ACTTCAGCAA CAACACGTAA TGTACGGTGG ATATTCGAAT CAGAACTACT ATCAACAGCC 2100
2101 TTCTGGTCGT CCGAAACGAT TTTCAGCAAC AGGGAAACAT GCCCTTTTCG GAACCTTCTC 2160
2161 AGCCCATGTT CAGCACCAAT TATATGAAAC AACAAGGATC ACAGCCGTCT TACAAGACCG 2220
2221 TCTGACCCAA CAGCAATCGC AACCTCAGTC GCATAATAAT CAATATTATC CGAATGGAGG 2280
2281 GTTACTGAT GTGCCCAACT TGAATTATCC AGCGACTCCA CCACCAACTC AAAGCATTTA 2340
2341 TTCACATAAC AACAACTCTA ATTCGAAGGT ATATCAATCC GCTCAGCATA CATCTCCCGG 2400
2401 TCAATATTCT GTTGCCAGTG AGTCCGGTTT GTACATCCCG CCACCACTGC AGCAACAGCA 2460
2461 GAATGGTCAA CAGAGTCCTG TGAGATCGGT ACATCAACAG ACACAGCAAA CACCGCCAAC 2520
2521 ATTTACTCAG CAACAAAGCT CTTCCCAACC TCAGTCACCT CAACACAATA CGTTATCATG 2580
2581 CACAGCAGCA GCAGCAGCAG CAGCAGCAGC AACAACAAAC TCAACAGGCC CAGCAGCAAG 2640
2641 GACAACGACA AACTCAGCAA CAGTCTCAGC AGCAAGCTCA ACAACAGAAT GGATCGGCGA 2700
2701 ATAATTACAT GTATTTGAG AGAAGACCTG ACCTATTGAC CAAAACTACC CAAGACAAAG 2760
2761 CAGATCGAAT TCCTGCAGCC CGGGGGATCC ACTAGTTCTA GAGCGGCCGC CACCGCGGTG 2820
2821 GAGCTCCAAT TCGCCCTATA GT                                           2842
        |    10    |    20    |    30    |    40    |    50    |    60
```

According to a preferred embodiment of the invention, the two DNA sequences defined under pants (b) and (c) above correspond in addition to the restriction map given in FIG. 3.

According to another preferred embodiment of the invention, the nucleic acid sequence described above is extracted from the E. coli strain DH5l recombined with the plasmid Ye23/31, deposited with the CNCM (Collection Nationale de Culture de Micro-organisms) Institut Pasteur, 25, rue du Docteur Roux, 75724 Paris Cedex 15, France in Paris, France in Jul. 2, 1991 under number I-1121.

In this context "complementary sequence" to a given nucleic acid sequence is said to be a reverse and complementary sequence to a given nucleotide sequence. The term "reverse" takes into account the restoration of the 5'-3' orientation of the nucleic acid which is also complementary to the given base sequence by the nature of the nucleotides it contains.

The 5.2 kb nucleic acid sequence comprises, in addition to the sequence coding for the said resistance protein described above, the DNA which may be designated by the term "cofactor", which determines the level of resistance to cycloheximide in K. lactis and in a cell host transformed by this sequence. This cofactor DNA is included in sequence ID NO: 3.

Thus the invention also relates to the following DNA fragments, included in the 5.2 kb sequence described above:

the BamHI (5')—PvuII (3') fragment of about 2.3 kb the PvuII (5')—SalI (3') fragment of about 3 kb.

The production of cycloheximide resistance in a given cell host at a defined level can be achieved by transforming this host with a nucleic acid coding for the cycloheximide resistance protein and with a cofactor DNA fragment present in the 5.2 kb sequence, adjacent or not adjacent to the above nucleic acid, the introduction of this fragment in the host being directly correlated with the level of resistance observed. One embodiment of the transformation of a cell host is described in the following pages.

The resistance protein can be isdated by lysis of the *K. lactis* cells followed by the steps desribed in "The Yeasts" (second edition by A. H. Rose and J. S. Harrison, vol. 4.4: 504–505).

The purification can also be clone by affinity using antibodies directed against the sequence A (SEQ. ID NO:2). In this case an over-expression of the ribosomal protein is produced which is then purified on polyacrylamide gel according to standard techniques. The molecular weight band corresponding to the sequence A protein is excised. This band is the major band because it results from the over-expression of the protein. It is subjected to reaction with the antibodies, in particular monoclonal antibodies, described above, produced according to standard procedures.

The invention also relates to the ORF A sequence containing nucleic acid (SEQ. ID NO:2), ORF A being itself included between the nucleotides at positions 1 and 1560 of sequence ID NO:3, it being understood that the sequence included between nucleotides 633 and 1222 corresponds to the intron V. The ORF A sequence contains two exons, one being formed by the nucleotides ATGG situated between nucleotides 629 and 632, the other exon being formed by the sequence included between nucleotides 1223 and 1539.

The nucleotide sequence included between nucleotides 1 and 1539 contains the promoter for the gene, in addition to the ORF A sequence.

Other particularly useful nucleotide sequences in the framework of the invention are the following sequences:
the nucleotide sequence ORF A as such or any nucleotide chain which hybridizing with the sequence complementary to ORF A under the following conditions: 60° C., 2×SSC, 5×Denhart, 0.1% SDS, 0.1 mg/ml salmon sperm DNA,
the coding sequence ID NO.2 (or exon) contained in the ORF A nucleic acid which codes for the resistance protein in *Kluyveromyces lactis*, and induded between nucleotides 629 and 1539, which forms a sequence of two exons one of which is included between nucleotides 629 and 632 and the other between nucleotides 1223 and 1539,
the sequence IV, comprising nucleotides 1561 and 2240 and which corresponds to the so-called cofactor sequence situated between nucleotides 1540 and 2763 and capable of increasing the cycloheximide resistance conferred by the resistance protein,
the intron V of ORF A,
the nucleotide sequence III defined by nucleotides 1 and 628, and more particularly by 8 and 628, which contains the regulatory elements af expression for ORF A and in particular the promoter region for the transcription of the ORF A sequence; this promoter contains in particular regulatory regions of the promoters for proteins characteristic ef the ribosomes, regions of the "UAS$_{RPG}$" type such as described by W. H. Mager (Biochem. Biophys. Acta (1988) 949: 1–15). These so-called ribosomal proteins are imported into the nucleus of the cell which produces them, where they are assembled into ribosomes,
the so-called cofactor sequence IV included between nucleotides 1561 and 2740 which is capable of increasing the resistance to cycloheximide conferred by the resistance protein.

The subject of the invention is also recombinant vectors in particular for cloning and/or expressing the proteins previously characterized.

These expression vectors are characterized by the incorporation, at one of their sites inessential for their replication, of a nucleotide sequence selected from those previously mentioned under the control of the regulatory elements necessary for its expression in a selected eukaryotic cell host, these regulatory elements comprising in particular an optionally inducible promoter and a transcription termination sequence.

Such a vector may comprise a nudeaide sequence coding for a protein called cycloheximide resistance protein, alone or in association with a cofactor nucleotide sequence complying with the previously given definition.

In addition, the invention relates to vectors complying with the above definitions characterized in that they contain in addition a specific heterologous nucleic add, for example a nucleic acid coding for a protein of industrial or pharmaceutical interest, this nucleic acid being under the control of regulatory elements necessary for its expression in the host, these elements being possibly fused with the sequences contrdling the transcription of the nucleotide sequences involved in cycloheximide resistance.

The resistance system according to the invention makes it possible to monitor advantageously the insertion of heterologous sequences such as that of human serum albumin, the surface antigen of hepatitis B virus, with a view to their expression in a eukaryotic host.

As examples, it is possible to use vectors of the replicating plasmid type, integrative vectors such as pSVL (Pharmacia). Such a vector may, for example, contain the nucleotide sequence coding for the protein corresponding to sequence A (SEQ. ID NO:2) without its intron.

Generally, it is useful for the implementation of the invention to use multiple-copy vectors, in particular when the transformed cells are eukaryotic cells.

Preferred vectors according to the invention are vectors suited for expression in yeasts, in particular of industrial importance, which it is desired to label with a resistance marker, for example when a auxotrophic marker is not available, a particular yeast being *Pichia pastoris* or *S. pombe*, or vectors suited for expression in a higher eukaryotic animal cell, for example baculovirus, or also vectors suited for expression in a plant cell such as tobacco plants. Thus simian cells or murine cells may be transformed.

A particularly advantageous vector in the framework of the invention is the plasmid Ye23/31 which transforms the *E. coli* strain DH51 deposited with the CNCM on Jul. 2, 1991 under the number I-1121.

Furthermore, the inventicn relates to a eukaryotic cell characterized in that it is transformed by a vector corresponding to the above characteristics and in particular in that it is a yeast cell, for example *Pichia pastoris*, a higher eukaryotic animal cell, for example an insect cell or a mammalian cell, in particular a murine or simian cell, a human cell or also a plant cell.

Such a recombinant cell may be obtained by all of the procedures for the insertion of heterologous sequences commonly used for the preparation of recombinant cell host. It is possible in particular to apply the electroporation procedure described by M. Becker, L. Garente in Methods in Enzymology (1991 vol. 194: 182–187).

It will also be possible to have recourse to the procedures described in the patent application WO 84/02913 on the subject of the insertion in to plant cells of nucleotide sequences heterologous with respect to the nucleic acids naturally contained in such cells.

As an application, the resistance proteins previously described can be used in a selection system corresponding specifically to a cycloheximide-type marker in order to monitor the introduction into a eukaryotic host of a heterologous sequence which it is desired to express in this host. The selection will be the easier if the resistance can be verified with a high concentration of antibiotic, this resistance then resulting from the association of the above resistance protein with a cofactor previously defined.

It is particularly interesting in the framework of the invention to prepare proteins which make it possible to obtain resistance at a cycloheximide concentration of about 100 µg/ml, even 1 mg/ml Furthermore, the invention relates to a procedure for monitoring the presence of a heterologous nucleic acid in a cell host, characterized in that it comprises:

the transformation of the cell host by an expression vector containing at one of its sites inessential for its replication the heterologous nucleic acid, on the one hand, a nucleotide sequence coding for a resistance protein, on the other, and optionally a cofactor nucleotide sequence under the control of the regulatory elements necessary for the expression of these sequences in a selected cell host, the culture of the cell host thus transformed, the placing of the host in contact with a defined concentration of cycloheximide and the detection of host resistance to this antibiotic.

The subject of the invention is also a method for obtaining cells which express cyloheximide resistance as described in the preceding pages, characterized by the following steps:

transformation of a given cell host by a nucleic acid sequence of the invention inserted beforehand in a host plasmid under conditions allowing the expression of the above-mentioned nucleic acid sequence;

culture of the transformed cells (transformants) in a complete medium containing a very low cycloheximide concentration, preferably lower than 2 µg/ml;

recovery of the resistant strains at a cycloheximide concentration higher than 1 to 10 µg/ml.

As an example, in respect to yeasts, the steps described above are performed under the following conditions:

the culture of the transformants is carried out at a temperature between about 29° C. and about 30° C., preferably 30° C., in the presence of a cycloheximide concentration lower than 2 µg/ml for 12 to 36 hours, the strains selected from this culture are those which are resistant culture in the presence of 100 µg/ml of cycloheximide, the complete culture medium contains 10 g/l of yeast extract, 20 g/l of Bacto peptone and 20 g/l of glucose.

The culture step of the transformants mentioned above is preferably carried out for 12 to 18 hours at 30° C. after transformation in a complete liquid medium at sub-limiting concentrations (1 µg/ml). This concentration may be adapted as a function of the strain and the species of yeast used.

In the case of eukaryotic cells as for example (mouse) LTK-cells, the culture medium may be Dulbecco medium supplemented with 10% newborn calf serum and by a fungicidal antibiotic.

The recombinant clones are selected according to the procedure described by Delpeyroux et al. in Journal of Virology (Dec 1990 vol.64 (12): 6090–6100).

In summary, the cells are cotransfected with 10 times more recombinant plasmid than vector containing the antibiotic resistance gene G418 (Colbère—Garapin F. et al, 1981, J. Mol. Bio. 150: 1–14). After three weeks, the resistant clones are placed in a culture medium supplemented with cycloheximide at a concentration of 1 to 10 µg/ml.

When the cell host is S. cerevisiae, the plasmid containing the nucleotide sequence of the invention may be an episomal multicopy plasmid of the YEp plasmid family, for example the 2µ plasmid of S. cerevisiae, or the episomal multicopy plasmid Ye 23/31.

Other advantages and characteristics of the invention will become apparent from the Examples and Figures which follow.

FIG. 1: Cloning Vector Containing the DNA Fragment of K. Lactic of About 5.2 kb Conferring Cycloheximide Resistance A genome library of the K. lactis strain 2359-152 resistant to several mg/ml of cycloheximide was constructed. This library is constructed in a shuttle vector E. coli/S. cerevisiae: pEMBL Ye 23 (Baldari et al. 1985 Gene 35: 27–32, FIG. 1). The chromosomal DNA of K. lactis was partially digested by the enzyme Sau3A, then fractionated on a sucrose gradient. The fractions containing DNA included a size between 4 and 9 kb were recovered and the DNA was ligated to the vector YE 23 previously cut and dephosphorylated at the BamHI site situated in the beta-galactosidase gene. This ligation mixture made it possible to transform the E. coli strain XL1 and the recombinant transformants were selected on a medium which allows an insertion in the beta-galactosidase gene to be visualized. 23000 recombinant E. coli clones were thus selected. Restriction analysis of the plasmids of fifty clones enabled the mean size of the DNA insertion in K. lactis to be estimated at 5 kb, which gives a 99.5% probability of obtaining a specific gene.

E. coli strain XL1 (strain developed by the Stratagene company): endA1, hsdR17 (rk⁻, mk⁺), supE44, thi⁻, λ⁻, recA1, gyrA96, relA1,Δ (lac), P, proAB, laciq Z M15, Tn10 (tet').

S. cerevisiae strain OL1: 1, leu2-3, leu2-112, his3-11, his3-15, ura3-251, ura3-273.

FIG. 2: Sequence fragment of the DNA of K. lactis conferring cycloheximide resistance (sequence ID NO:3).

FIG. 3: restriction map of the 5.2 kb DNA fragment of K. lactis which was inserted at the BamHI site of the vector Ye 23 (C. Baldari et al., Gene (1985) 35: 27).

The sequenced SalI-PvuII fragment (2.8 kb) contains the ribosomal protein. The various sites are situated respectively at the following positions:

Sau3A: 0, StuI: +300 bp, PvuII: +600 bp, BglIII: +900 bp, BstXI: +1200 bID, PvuII: +2300, PstI: +2400 bp, PstI: +3000 bp, EcoRI: +3200 bp, HindIII: +3300 bp, EcoRI: +3700 bp, HindIII: +4500 bp, HindIII: +4540 bp, SalI: +5100 bp.

FIG. 4, SEQ ID NO:2: Protein conferring cycloheximide resistance, encoded in K. lactis DNA.

EXAMPLES

I Cloning of the DNA Fragment of K. lactis Conferring Cycloheximide Resistance

I.1) Construction of a K. lactis Library in S. cerevisiae:

A genome library of the K. lactis strain 2359-152 (WESOLOWSKI et al., 1982, Curr. Genetics 5: 191–197)

resistant to concentrations of several mg/ml of cycloheximide was created. This library was constructed in a shuttle vector E. coli/S. cerevisiae: pEMBL YE 23 (BALDARI et al., 1985, Gene 35: 27–32) (FIG. 1). K. lactis chromosomal DNA was partially digested by the enzyme Sau3A, then fractionated on a sucrose gradient. The fractions containing DNA of a size included between 4 and 9 kb were recovered and ligated to the vector YE 23 previously cut and dephosphorylated at the BamI-II site situated in the beta-galactosidase gene. This ligation mixture made it possible to transform the E. coli XL1 strain (BULLOCK et al., 1987, Biotechniques 5, 376–379) and the recombinant transformants were selected on a medium which allows an insertion in the beta-galactosidase gene to be visualized. 23000 recombinant E. coli clones were thus selected. Restriction analysis of the plasmids of fifty clones enabled the mean size of the DNA insertion in K. lactis to be estimated at 5 kb, which gives a 99.5% probability of obtaining a specific gene.

I.2) Transformation of S. cerevisiae and Production of Cycloheximide Resistant Transformants The S. cerevisiae strain OL1 (BOY-MARCOTTE et al., 1982, Gene 20: 433–440), sensitive to cycloheximide concentrations lower than 1 μg/ml, was transformed with the DNA extracted from the library. In a first stage, the transformants were screened for uracil prototrophy which enabled the total number of transformants to be evaluated. In a second stage these transformants were subcultured on a medium containing cycloheximide at two concentrations: 10 and 100 ug/ml. 3500 URA$^+$ transformants were obtained, 7 of which are resistant to cycloheximide concentrations higher than 100 ug/ml. After analysis, it emerged that 6 of the 7 clones retained had integrated the DNA derived from K. lactis in to their genome. However, in the seventh transformant the resistance character was maintained on the Ye 23/31 plasmid derived from the pEMBLYe23 vector. This transformant is resistant to very high cycloheximide concentrations, in excess of 1 mg/ml. The DNA fragment conferring cycloheximide resistance is about 5.2 kb.

Furthermore, for the transformants which have integrated the K. lactis DNA fragment into their genome, the resistance phenomenon is maintained in a diploid, heterozygous for this marker. The "cycloheximide resistant" character is thus dominant.

I.3) Protein Responsible for Cycloheximide Resistance

This entire fragment was inserted into pBluescript phagemid vectors (Stratagene). Different unidirectional deletions were constructed with the aid of the enzyme couple ExoIII/S1. The sequencing of the single-stranded DNA was carried out with the aid of the Sanger procedure by using universal primers or primers synthesized in the laboratory from the sequence itself.

A fragment of the sequence thus obtained is shown in FIG. 2. It contains in particular an open reading frame ORF A

ORF A:

This open reading frame is 320 bp long (FIG. 2) and carries an intron of 590 bp. This intron is located at the 5' end of the gene, after the first base after the ATG. The protein encoded by the exon contains 150 amino acids (FIG. 4). The search for hornologies with the aid of the EMBL and GENEBANK data banks shows that the ORF A has a 75% hornology at the amino acid level with the ribosornal protein L36a of the rat (GALLAGHER et al., 1988, DNA 7: 269–273) and 74% hornology with a human ribosomal protein (DAVIES et al., 1986, Gene 45: 183–191) which is itself homologous with the ribosomal protein rp44 (also designated L41) of S. cerevisiae (ITOH, 1978 FEBS Lett. 96:399–402).

This sequence is sufficient to confer a high level of cycloheximide resistance; however, this level is lower than that observed in the transformants possessing the initial 5.2 kb fragment.

I.4) Expression of the Open Reading Frame A

In order to determine to what extent the so-called resistance protein is responsible for the cyd oheximide resistance phenomenon, the same S. cerevisiae strain was transformed under the same conditions with a vector containing only the ORF A. The transformants which possess the ORF A are resistant to cycloheximide. However, the level of resistance observed (100 μg/ml) is about ten times lower than that obtained when the ORF A is associated with the cofactor DNA contained in the entire fragment of 5.2 kb (1000 μg/ml). On the other hand, the deletion of the ORF A sequence leads to the abolition of resistance.

CONCLUSIONS

A gene responsible for the phenomenon of cycloheximide resistance was isolated from a DNA fragment of K. lactis. This system is composed of a ribosomal protein (ORF A) very dosely analogous to the human L36a and rat ribosomal proteins as well as to rp44 (or L41) of S. cerevisiae. This protein is necessary to cause the phenomenon of resistance but is not sufficient to have complete resistance to the antibiotic. The presence of a cofactor located on the cloned 5. 2 kb fragment of K. lactis is necessary to obtain resistance at about the 1 mg/ml level in K. lactis.

We claim:

1. A nucleic acid sequence of *Kluyveromyces lactis* of about 5.2 kb which confers resistance to cycloheximide at a concentration higher than 100 µg/ml on *Kluyveromyces lactis* or on *Saccharomyces cerevisiae*, wherein said nucleic acid sequence comprises the following restriction sites: Sau3A: 0, StuI: +300 bp, PvuII: +600 bp, BglIII : +900 bp, BstXI: +1200 bp, PvuII: +2300, PstI: +2400 bp, PstI: +3000 bp, EcoRI: +3200 bp, HindIII: +3300 bp, EcoRI: +3700 bp, HindIII: +4500 bp, HindIII: +4540 bp, SalI: +5100 bp.

2. The nucleic acid sequence according to claim 1, comprising one of the following sequences:
   (1) SEQ ID NO:2; or
   (2) a sequence which hybridizes to a sequence complementary SEQ ID NO:2 under conditions of high stringency, and confers resistance to cycloheximide at a concentration higher than 1 mg/ml in *Kluyveromyces lactis*.

3. The nucleic acid sequence of claim 1, comprising one of the following sequences:
   (1) SEQ ID NO:3; or
   (2) a sequence which hybridizes to a sequence complementary SEQ ID NO:3 under conditions of high stringency, and confers resistance to cycloheximide at a concentration higher than 1 mg/ml in *Kluyveromyces lactis*.

4. The nucleic acid sequence according to claim 1, comprising one of the following sequences:
   (1) nucleotides 9-2763 of SEQ ID NO:3; or
   (2) a sequence which hybridizes to a sequence complementary to nucleotides 9-2763 of SEQ ID NO:3 under conditions of high stringency, and confers resistance to cycloheximide at a concentration higher than 1 mg/ml in *Kluyveromyces lactis*.

5. A nucleotide sequence according to claim 3, comprising one of the following sequences:
   (1) nucleotides 1-1560 of SEQ ID NO:3; or
   (2) a nucleotide sequence which hybridizes to a sequence complementary to nucleotides 1-1560 of SEQ ID NO:3 under conditions of high stringency.

6. The nucleotide sequence according to claim 5, comprising SEQ ID NO:2.

7. The nucleotide sequence according to claim 6, comprising (1) nucleotides 1-628 of SEQ ID NO:3; or (2) a promoter region for transcription of nucleotides 1-1560 of SEQ ID NO:3.

8. A nucleotide sequence which increases the cycloheximide resistance conferred by a protein encoded by the nucleotide sequence according to claim 1, wherein said nucleotide sequence which increases cycloheximide resistance comprises nucleotides 1561-2740 of SEQ ID NO:3, provides resistance to cycloheximide at a concentration higher than 100 µg/ml in a eukaryotic host cell transformed with (1) said nucleotide sequence; and (2) a nucleotide sequence encoding SEQ ID NO:1, under conditions suitable for the production of protein encoded by SEQ ID NO:1.

9. A recombinant vector for cloning and/or expression of a nucleotide sequence, comprising the nucleotide sequence according to claim 1, under the control of regulatory elements comprising a promoter and a transcription termination sequence.

10. The vector according to claim 9, wherein said vector is suited for expression in a eukaryotic host cell.

11. The vector according to claim 10, wherein said eukaryotic host cell is a yeast, an animal cell or a plant cell.

12. The vector according to claim 11, wherein said yeast is *Pichia pastaris*.

13. The vector according to claim 11, wherein said vector is baculovirus.

14. The vector according to claim 9, wherein said promoter is inducible.

15. The vector according to claim 9, further comprising a nucleic acid to be expressed in a eukaryotic host cell, said nucleic acid being under the control of regulatory elements necessary for its expression in the host cell.

16. The vector according to claim 9, wherein said vector is contained in an *E. coli* strain deposited with the CNCM on Jul. 2, 1991, under the number I-1121.

17. A method for monitoring successful transformation of a host cell, comprising:
   (1) transforming a eukaryotic host cell sensitive to cycloheximide with the vector of claim 9;
   (2) culturing said eukaryotic host cell in the presence of cycloheximide;
   (3) identifying a eukaryotic host cell which is resistant to cycloheximide; and
   (4) correlating the resistance to cycloheximide of said eukaryotic host cell with the successful transformation of said eukaryotic host cell.

18. The method of claim 17, wherein said vector comprises a sequence encoding a heterologous protein at a site inessential for replication of said vector, wherein said sequence encoding the heterologous protein is under the control of regulatory elements necessary for the expression of said sequence in the host cell.

19. The method of claim 18, wherein the presence of the sequence encoding the heterologous protein is detected.

20. The nucleotide sequence according to claim 1, wherein said nucleotide sequence is obtained from an *E. coli* strain DH5 transformed by the plasmid Ye23/31 deposited with the CNCM on Jul. 2, 1991, under the number I-1121.

21. A nucleotide sequence comprising SEQ ID NO:3, or a nucleotide sequence which hybridizes to a sequence complimentary to SEQ ID NO:3 under conditions of high stringency, provided that the nucleotide sequence possesses at least one the properties selected from the group consisting of: (1) coding for a cycloheximide resistance protein; or (2) coding for an amino acid sequence which is recognized by antibodies directed against a cycloheximide resistance protein and provides cycloheximide resistance in *Kluyveromyces lactis*.

22. A eukaryotic host cell wherein said cell is transformed by a vector according to claim 9.

23. The eukaryotic host cell of claim 22, wherein said cell is selected from the group consisting of a yeast cell, an animal cell and a plant cell.

24. The nucleic acid sequence of claim 2, wherein said nucleic acid sequence confers resistance to cycloheximide at a concentration higher than 1 mg/ml in *Kluyveromyces lactis*.

* * * * *